United States Patent [19]

Gutman

[11] 3,984,410
[45] Oct. 5, 1976

[54] ISOUREA ACETYLPHOSPHATE INSECTICIDES

[75] Inventor: Arnold D. Gutman, Berkeley, Calif.

[73] Assignee: Stauffer Chemical Company, Westport, Conn.

[22] Filed: Dec. 10, 1975

[21] Appl. No.: 639,318

[52] U.S. Cl. .................. 260/247.1 B; 424/200; 424/211; 260/247.2 H; 260/247.5 R; 260/293.85; 260/561 HL; 260/564 E; 260/943

[51] Int. Cl.² .................. C07F 9/165; C07F 9/65

[58] Field of Search ............... 260/247.1 B, 293.85, 260/943

[56] References Cited
UNITED STATES PATENTS

| | | | |
|---|---|---|---|
| 2,959,610 | 11/1960 | Young et al. | 260/943 |
| 3,134,801 | 5/1964 | Sehring et al. | 260/943 |
| 3,259,540 | 7/1966 | Pianka et al. | 260/943 |
| 3,896,190 | 7/1975 | Beutel et al. | 260/247.1 B |

*Primary Examiner*—Natalie Trousof
*Assistant Examiner*—R. W. Ramsuer
*Attorney, Agent, or Firm*—Daniel C. Block

[57] ABSTRACT

Compounds are described herein which are useful as insecticides, and which are defined by the following formula

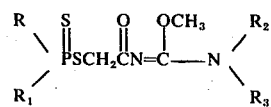

wherein R is lower alkoxy, $R_1$ is lower alkyl or lower alkoxy, $R_2$ is allyl or lower alkyl, and $R_3$ is selected from the group consisting of allyl, lower alkyl, phenyl, benzyl, and 3-methylphenyl; or $R_2$ and $R_3$ taken together are $-CH_2(CH_2)_3CH_2-$ or $-CH_2CH_2OCH_2CH_2-$.

21 Claims, No Drawings

ISOUREA ACETYLPHOSPHATE INSECTICIDES

BACKGROUND AND BRIEF DESCRIPTION OF THE INVENTION

The utility of thiophosphorus compounds is well known in the field of insecticides and acaricides. This invention relates to a novel class of such compounds and to their use as insecticides when used in an insecticidally effective amount. More specifically, this invention relates to isourea acetylphosphate compounds having the formula

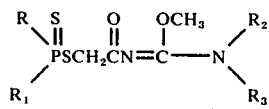

wherein R is lower alkoxy, $R_1$ is lower alkyl or lower alkoxy, $R_2$ is allyl or lower alkyl, and $R_3$ is selected from the group consisting of allyl, lower alkyl, phenyl, benzyl, and 3-methylphenyl; or $R_2$ and $R_3$ taken together are —$CH_2(CH_2)_3CH_2$— or —$CH_2CH_2OCH_2CH_2$—.

By "lower alkyl" is meant straight- or branched-chain alkyl groups containing from 1 to 4 carbon atoms, inclusive. By "lower alkoxy" is meant straight- or branched-chain alkoxy groups having from 1 to 4 carbon atoms, inclusive.

By "insecticidally effective amount" is meant the amount of the herein disclosed insecticidal compounds which when applied to the habitat of insects in any conventional manner will kill or substantially injure a significant portion of the population thereon.

DETAILED DESCRIPTION OF THE INVENTION

The compounds of the present invention can be prepared as follows:

The properly selected N,N-disubstituted cyanamide is reacted with methanol in the presence of KCN to yield the corresponding O-methyl iminoether. The latter is reacted with chloroacetyl chloride in the presence of an acid acceptor in an inert solvent to produce a chloro-acetylated iminoether, which is in turn reacted with the properly selected dithiophosphoric acid in the presence of an acid acceptor to yield the desired product.

The examples shown herein are illustrative of the method of preparation described hereinabove. The compound numbers refer to Table I which is a further listing of the compounds which are representative of those embodied in the present invention.

EXAMPLE I

N,N-Diallyl-N'-(O,O-diethylphosphorodithioylacetyl)-O-methylisourea (Compound No. 1 in Table I below)

A. The following reactants were combined in a 1-liter, round-bottom flask: 24.4 g (0.2 mole) diallyl-cyanamide, 13 g (0.2 mole) KCN and 500 ml methanol. The mixture was heated under reflux for 24 hours, then stripped in vacuo. The residue was dissolved in 250 ml $H_2O$, which was subsequently extracted with three 200 ml portions of diethyl ether. The organic phases were combined, washed with 200 ml of $H_2O$ and dried with $MgSO_4$. The solvent was evaporated to yield 20.7 g (67% yield) of N,N-diallyl-O-methyl isourea.

B. The isourea, 7.7 g (0.05 mole), was combined with 150 ml of tetrahydrofuran in a 500 ml three-neck flask. The solution was stirred and cooled in an ice-acetone bath to 10°C. Chloroacetyl chloride, 4 ml, 5.65 g (0.05 mole), was added drop-wise to the solution at such a rate that the temperature did not exceed 10°C. Following the addition, 69 ml, 5.05 g (0.05 mole) of triethyl amine was added drop-wise to the solution while the temperature was again maintained below 10°C. The resulting mixture was stirred at room temperature for 1 hour, then stirred for an additional hour at 45°C. The mixture was subsequently poured into 300 ml of benzene and washed with 150 ml of ice water. The organic phase was dried with $MgSO_4$, and the solvent was evaporated to yield 10.4 g (90% yield) of N,N-diallyl-N'-(chloroacetyl)-O-methylisourea, $n_D^{30}$ 1.4800, confirmed by NMR analysis.

C. In a 150 ml beaker were placed 3.2 g (0.017 mole) diethyl dithiophosphoric acid, an excess of $K_2CO_3$, and 50 ml of acetone. The mixture was stirred until neutralized. The acetone was then decanted into a 200 ml round-bottom flask containing 3.5 g (0.015 mole) of the chloroacetyl isourea prepared in Step B above, in 25 ml of acetone. After about 5 minutes salt began to form and the mixture was stoppered and set aside. Several hours later the mixture was poured into 200 ml of benzene, washed with two 100 ml portions of $H_2O$, dried and evaporated. The yield was 5.1 g (89% yield) of N,N-diallyl-N'-(O,O-diethylphosphorodithioylacetyl)-O-methylisourea, $n_D^{30}$ 1.5004, confirmed by NMR spectroscopy.

EXAMPLE II

N-morpholino-N'-(o,o-diethylphosphorodithioylacetyl)-o-methylisourea (Compound No. 4 in Table I below)

In the same manner as Example IA above, 31.1 g (0.278 mole) of N-cyanomorpholine, 18.1 g (0.278 mole) of potassium cyanide and 500 ml of methanol were combined to yield 39.6 g (99% yield) of N-morpholino-O-methylisourea, $n_D^{30}$ 1.5327.

Following the procedure of Example IB, 7.2 g (0.05 mole) of the above isourea, 5.65 g (0.05 mole) of chloroacetyl chloride, 5.05 g (0.05 mole) of triethyl amine and 150 ml of tetrahydrofuran were combined to yield 11.6 g of N-morpholino-N'-(chloroacetyl)-O-methylisourea, $n_D^{30}$ 1.4853.

The procedure of Example IC was then followed, using 4 g (0.018 mole) of the above chloro-acetylated product, 3.72 g (0.02 mole) of diethyl dithiophosphoric acid, 5 g of potassium carbonate, and 200 ml of acetone were combined to yield 5.0 g (75% yield) of N-morpholino-N'-(O,O-diethylphosphorodithioylacetyl)-O-methylisourea, $n_D^{30}$ 1.5117, confirmed by NMR spectroscopy.

The compounds in the above examples are listed in Table I together with other compounds which are representative of the types of compounds embodied in the present invention. The methods of preparation for all of the compounds in Table I as well as for those of the entire genus of which the Table I compounds are representative are analogous to those exemplified in the examples above, when the appropriate starting materials are used.

TABLE I $$\begin{array}{c} R \\ \diagdown \\ \phantom{P}\diagup \\ R_1 \end{array} \overset{S}{\underset{\|}{P}}\text{SCH}_2\text{CN}=\overset{OCH_3}{\underset{|}{C}}\text{---N}\begin{array}{c} R_2 \\ \diagup \\ \diagdown \\ R_3 \end{array}$$

| Compound No. | R | $R_1$ | $R_2$ | $R_3$ | $n_D^{30}$ |
|---|---|---|---|---|---|
| 1 | $C_2H_5O$ | $C_2H_5O$ | allyl* | allyl | 1.5004 |
| 2 | $CH_3O$ | $CH_3O$ | allyl | allyl | 1.5034 |
| 3 | $C_2H_5O$ | $C_2H_5O$ | —CH$_2$(CH$_2$)$_3$CH$_2$— | | 1.5127 |
| 4 | $C_2H_5O$ | $C_2H_5O$ | —CH$_2$CH$_2$OCH$_2$CH$_2$— | | 1.5117 |
| 5 | $C_2H_5O$ | $C_2H_5O$ | $C_2H_5$ | $C_2H_5$ | 1.4968 |
| 6 | $CH_3O$ | $CH_3O$ | $C_2H_5$ | $C_2H_5$ | 1.4998 |
| 7 | $C_2H_5O$ | $C_2H_5$ | $C_2H_5$ | $C_2H_5$ | 1.5135 |
| 8 | $C_2H_5O$ | $C_2H_5O$ | $CH_3$ | $C_6H_5$ | 1.5280 |
| 9 | $C_2H_5O$ | $C_2H_5$ | $CH_3$ | $C_6H_5$ | 1.5342 |
| 10 | $C_2H_5O$ | $C_2H_5O$ | allyl | $C_6H_5$ | 1.5157 |
| 11 | $CH_3O$ | $CH_3O$ | allyl | $C_6H_5$ | 1.5173 |
| 12 | $C_2H_5O$ | $C_2H_5O$ | $CH_3$ | —CH$_2$C$_6$H$_5$ | 1.5250 |
| 13 | $CH_3O$ | $CH_3O$ | $CH_3$ | —CH$_2$C$_6$H$_5$ | 1.5285 |
| 14 | $C_2H_5O$ | $C_2H_5$ | $CH_3$ | —CH$_2$C$_6$H$_5$ | 1.5443 |
| 15 | $C_2H_5O$ | $C_2H_5O$ | $C_2H_5$ | $C_6H_5$ | 1.5245 |
| 16 | $CH_3O$ | $CH_3O$ | $C_2H_5$ | $C_6H_5$ | 1.5240 |
| 17 | $C_2H_5O$ | $C_2H_5$ | $C_2H_5$ | $C_6H_5$ | 1.5292 |
| 18 | $C_2H_5O$ | $C_2H_5O$ | $C_2H_5$ | 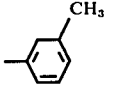 | 1.5183 |
| 19 | $CH_3O$ | $CH_3O$ | $C_2H_5$ | 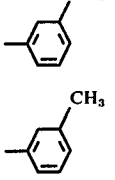 | 1.5143 |
| 20 | $C_2H_5O$ | $C_2H_5$ | $C_2H_5$ | (2-methylphenyl) | 1.5378 |

*allyl: —CH$_2$CH=CH$_2$

Insecticide Evaluation

A. Housefly (Musca domestica L.)

Test compounds are diluted in acetone and aliquots are pipetted onto the bottom of 55 × 15 mm aluminum dishes. To insure even spreading of the chemical on the bottom of the dishes, 1 ml of acetone containing 0.02% peanut oil is also added to each dish. After all solvents have evaporated the dishes are placed in circular cardboard cages containing 25 3-day old female houseflies. The cages are covered on the bottom with cellophane and the top with tulle netting, and each contains a sugar-water saturated cotton plug for maintenance of the flies. Mortality is recorded after 48 hours. Test levels range from 100 μg/25 F. houseflies down to that at which approximately 50% mortality occurs.

B. Green Peach Aphid [Myzus persicae (Sulzer)]

Radish plants (Rhaphanus sativus), approximately 2 cm tall, are transplanted into sandy loam soil in 3-inch clay pots and infested with 25–50 green peach aphids of mixed ages. Twenty-four hours later they are sprayed, to the point of runoff, with 50—50 acetone-water solutions of the test chemicals. Treated plants are held in the greenhouse and mortality is recorded after 48 hours. Test concentrations range from 0.05% down to that at which 50% mortality occurs.

C. Direct Spray Assay on Black Bean Aphid [Aphis fabae (Scop.)]

Nasturtium plants (Tropaeolum sp.), approximately 5 cm tall, are transplanted into sandy loam soil in 3-inch clay pots and infested with 25–50 black bean aphids of mixed ages. Twenty-four hours later they are sprayed, to the point of runoff, with 50—50 acetone-water solutions of the test chemicals. Treated plants are held in the greenhouse and mortality is recorded after 7 days. Test concentrations range from 0.05% down to that at which 50% mortality occurs.

D. Systemic Assay on Black Bean Aphid [Aphis fabae (Scop.)]

Test chemicals are diluted in acetone and aliquots are thoroughly mixed into 500 grams of dry, sandy loam soil. The treated soil is placed in a pint ice cream carton and a nasturtium plant (Tropaeolum sp.) approximately 5 cm tall is transplanted into each carton. The plants are then infested with approximately 25 black bean aphids of mixed ages and placed in the greenhouse. Seven days later mortality is recorded. Test concentrations range from 10 PPM down to that at which approximately 50% mortality occurs.

E. Lygus Bus [Lygus hesperus (Knight)]

Test compounds are in a 50—50 acetone-water solution. Two cc of the solutions are sprayed through a Devilbiss type EGA hand spray gun into circular cardboard cages containing one string bean pod and ten adult lygus bugs. The test cages are covered on the bottom with cellophane and the top with tulle netting. Percent mortality is recorded 48 hours later. Test concentrations range from 0.05% down to that at which approximately 50% mortality occurs.

F. German Cockroach [Blattella germanica (Linné)]

Test compounds are diluted in a 50—50 acetone-water solution. Two cc of the solutions are sprayed through a DeVilbiss type EGA hand spray gun into circular cardboard cages containing 10 1-month-old German cockroach nymphs. The test cages are covered on the bottom with cellophane and the top with tulle netting. Percent mortality is recorded 7 days later. Test concentrations range from 0.1% down to that at which approximately 50% mortality occurs.

G. Salt-Marsh Caterpiller [Estigmene acrea (Drury)]

Test compounds are diluted in a 50—50 acetone-water solution. Sections of curly dock (Rumex crispus) leaves, approximately 1 × 1.5 inches, are immersed in the test solutions for 2–3 seconds and placed on a wire screen to dry. The dried leaves are placed in petri dishes containing a moistened piece of filter paper and infested with five second-instar salt-marsh larvae. Mortality of the larvae is recorded 48 hours later, and a piece of synthetic media is added to dishes containing survivors. These are then held for 5 additional days to observe for any delayed effects of the test chemicals. Test concentrations range from 0.1% down to that at which approximately 50% mortality occurs.

H. Cabbage Looper [Trichoplusia ni (Hübner)]

Test compounds are diluted in a 50—50 acetone-water solution. Cotyledons of hyzini squash (Calabacita abobrinha), approximately 1 × 1.5 inches, are immersed in the test solutions for 2–3 seconds to dry on a wire screen to dry. The dried leaves are placed in petri dishes containing a moistened piece of filter paper and infested with five second-instar cabbage looper larvae. Mortality of the larvae is recorded 48 hours later, and a piece of synthetic media is added to dishes containing survivors. These are then held for 5 additional days to observe for any delayed effects of the test chemicals. Test concentrations range from 0.1% down to that at which approximately 50% mortality occurs.

I. Tobacco Budworm [Heliothis virescens (F.)]

The procedure is the same as that used for the cabbage looper, except that sections of Romaine lettuce (*Latica sativa*) leaves were used instead of cotyledons of hyzini squash.

J. Southern House Mosquito [*Culex pipiens quinquefasciatus* (Say)]

Insecticidal activity is determined using third-instar larvae of the mosquito (*Culex pipiens quinquefasciatus*). Ten larvae are placed in a 6-ounce, number 67 Dixie wax paper cup containing 100 ml of an aqueous solution of the test chemical. The treated larvae are stored at 70°F, and 48 hours later the mortality is recorded. Test concentrations range from 0.5 PPM down to that at which approximately 50% mortality occurs.

The results of these tests on the compounds listed in Table I are shown in Table II below.

TABLE II

Insecticide Activity - Approximate $LD_{50}$ Values

| | |
|---|---|
| HF | Housefly |
| GPA | Green Peach Aphid |
| BA | Black Bean Aphid - direct spray |
| BAS | Black Bean Aphid - systemic |
| LB | Lygus Bug |
| GR | German Cockroach |
| SMC | Salt-marsh Caterpillar |
| CL | Cabbage Looper |
| TBW | Tobacco Budworm |
| MOS | Southern House Mosquito |

| Compound No. | HF μg/25 F. | GPA % | BA % | BAS ppm | LB % | GR % | SMC % | CL % | TBW % | MOS ppm |
|---|---|---|---|---|---|---|---|---|---|---|
| 1 | 10 | >.05 | .003 | 3 | .05 | >.1 | .05 | — | — | 1 |
| 2 | 8 | — | .008 | 5 | >.05 | >.1 | >.05 | — | — | >1 |
| 3 | 25 | .008 | .001 | >10 | .05 | >.1 | >.05 | >.1 | >.1 | 1 |
| 4 | 27 | >.05 | .0008 | 5 | .05 | >.1 | >.05 | — | — | >1 |
| 5 | 23 | .03 | .001 | >10 | >.05 | .1 | >.1 | >.1 | >.1 | >1 |
| 6 | 24 | >.05 | .05 | — | >.05 | >.1 | >.1 | >.1 | >.1 | >1 |
| 7 | 6.3 | .003 | .0003 | 1 | .003 | .08 | .1 | .005 | >.1 | >1 |
| 8 | 30 | .03 | .0008 | >1 | >.05 | >.05 | >.1 | >.1 | .1 | >1 |
| 9 | 10 | .003 | .0001 | >10 | .005 | .05 | >.1 | >.1 | >.1 | 1 |
| 10 | 10 | — | >.05 | — | .05 | >.1 | .03 | >.1 | >.1 | >1 |
| 11 | 30 | .03 | .005 | >10 | >.05 | >.1 | >.1 | >.1 | >.1 | >1 |
| 12 | 24 | — | >.05 | — | >.05 | >.1 | >.05 | >.1 | >.1 | >1 |
| 13 | 30 | — | >.05 | — | >.05 | >.1 | .05 | >.1 | >.1 | >1 |
| 14 | 3.8 | .002 | .005 | 10 | .05 | .005 | .05 | >.1 | >.1 | >1 |
| 15 | 30 | .03 | .005 | 2 | >.05 | >.1 | >.05 | .1 | >.1 | >1 |
| 16 | 25 | — | .03 | >10 | >.05 | >.1 | >.05 | .1 | >.1 | >1 |
| 17 | 7 | .002 | .001 | 3 | .05 | .02 | >.05 | >.1 | >.1 | >1 |
| 18 | 22 | .005 | .0005 | 5 | >.05 | .1 | >.05 | >.1 | .1 | >1 |
| 19 | 62 | .03 | .002 | >10 | >.05 | >.1 | >.05 | >.1 | >.1 | >1 |
| 20 | 5 | .001 | .0002 | 2 | .01 | .03 | .03 | >.1 | >.1 | >1 |

The compositions of this invention are generally embodied in forms suitable for convenient application. For example, the compositions can be incorporated into pesticidal formulations which are provided in the form of emulsions, suspensions, solutions, dusts, and aerosol sprays. In general, such formulations will contain, in addition to the active compound, the adjuvants which are found normally in pesticide preparations. In these formulations, the active compounds of this invention can be employed either as the sole pesticide component or in admixture with other compounds having similar utility. The pesticide formulations of this invention can contain, as adjuvants, organic solvents, such as sesame oil, xylene range solvents, heavy petroleum, etc.; water; emulsifying agents; surface active agents; talc; pryophyllite; diatomite; gypsum; clays; or propellants, such as dichlorodifluoromethane, etc. If desired, however, the active compositions can be applied directly to the feed stuffs, seeds, etc., upon which the pests feed. When applied in such a manner, it will be advantageous to use a composition which is not volatile. In connection with the activity of the presently disclosed pesticidal compositions, it should be fully understood that it is not necessary that they be active as such. The purposes of this invention will be fully served if the composition is rendered active by external influences, such as light, or by some physiological action which occurs when the preparation is ingested or penetrates into the body of the pest.

The precise manner in which the pesticidal compositions of this invention are used in any particular instance will be readily apparent to a person skilled in the art. Generally, the active pesticidal composition will be embodied in the form of a liquid composition; for example, an emulsion, suspension, or aerosol spray. While the concentration of the active pesticide composition in the present formulation can vary within rather wide limits, ordinarily, the pesticide composition will comprise not more than about 50.0% by weight of the formulation.

What is claimed is:

1. A compound having the formula

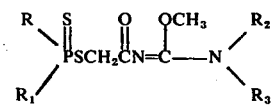

wherein R is lower alkoxy, $R_1$ is lower alkyl or lower alkoxy, $R_2$ is allyl or lower alkyl, and $R_3$ is selected from the group consisting of allyl, lower alkyl, phenyl, benzyl, and 3-methylphenyl; or $R_2$ and $R_3$ taken together are $-CH_2(CH_2)_3CH_2-$ or $-CH_2CH_2OCH_2CH_2-$.

2. The compound according to claim 1 in which R is ethoxy, $R_1$ is ethoxy, $R_2$ is allyl and $R_3$ is allyl.

3. The compound according to claim 1 in which R is methoxy, $R_1$ is methoxy, $R_2$ is allyl, and $R_3$ is allyl.

4. The compound according to claim 1 in which R is ethoxy, $R_1$ is ethoxy, and $R_2$ and $R_3$ taken together are $-CH_2(CH_2)_3CH_2-$.

5. The compound according to claim 1 in which R is ethoxy, $R_1$ is ethoxy, and $R_2$ and $R_3$ taken together are $-CH_2CH_2OCH_2CH_2-$.

6. The compound according to claim 1 in which R is ethoxy, $R_1$ is ethoxy, $R_2$ is ethyl, and $R_3$ is ethyl.

7. The compound according to claim 1 in which R is methoxy, $R_1$ is methoxy, $R_2$ is ethyl, and $R_3$ is ethyl.

8. The compound according to claim 1 in which R is ethoxy, $R_1$ is ethyl, $R_2$ is ethyl, and $R_3$ is ethyl.

9. The compound according to claim 1 in which R is ethoxy, $R_1$ is ethoxy, $R_2$ is methyl, and $R_3$ is phenyl.

10. The compound according to claim 1 in which R is ethoxy, $R_1$ is ethyl, $R_2$ is methyl, and $R_3$ is phenyl.

11. The compound according to claim 1 in which R is ethoxy, $R_1$ is ethoxy, $R_2$ is allyl, and $R_3$ is phenyl.

12. The compound according to claim 1 in which R is methoxy, $R_1$ is methoxy, $R_2$ is allyl, and $R_3$ is phenyl.

13. The compound according to claim 1 in which R is ethoxy, $R_1$ is ethoxy, $R_2$ is methyl, and $R_3$ is benzyl.

14. The compound according to claim 1 in which R is methoxy, $R_1$ is methoxy, $R_2$ is methyl, and $R_3$ is benzyl.

15. The compound according to claim 1 in which R is ethoxy, $R_1$ is ethyl, $R_2$ is methyl, and $R_3$ is benzyl.

16. The compound according to claim 1 in which R is ethoxy, $R_1$ is ethoxy, $R_2$ is ethyl, and $R_3$ is phenyl.

17. The compound according to claim 1 in which R is methoxy, $R_1$ is methoxy, $R_2$ is ethyl, and $R_3$ is phenyl.

18. The compound according to claim 1 in which R is ethoxy, $R_1$ is ethyl, $R_2$ is ethyl, and $R_3$ is phenyl.

19. The compound according to claim 1 in which R is ethoxy, $R_1$ is ethoxy, $R_2$ is ethyl, and $R_3$ is 3-methylphenyl.

20. The compound according to claim 1 in which R is methoxy, $R_1$ is methoxy, $R_2$ is ethyl, and $R_3$ is 3-methylphenyl.

21. The compound according to claim 1 in which R is ethoxy, $R_1$ is ethyl, $R_2$ is ethyl, and $R_3$ is 3-methylphenyl.

* * * * *